July 2, 1957 M. J. MURRAY Plant Pat. 1,612

MINT PLANT

Filed Aug. 29, 1955

INVENTOR.
MERRITT J. MURRAY
BY Lindley E. Mills

United States Patent Office

Plant Pat. 1,612
Patented July 2, 1957

1,612

MINT PLANT

Merritt J. Murray, Kalamazoo, Mich., assignor to A. M. Todd Company, Kalamazoo, Mich., a corporation of Michigan Application August 29, 1955, Serial No. 531,306

1 Claim. (Cl. 47—59)

This invention relates to a new and distinct variety of mint plant which was initially produced by hybridization between *Mentha piperita* L. and *Mentha arvensis* L. *piperascens* Briq. and thereafter asexually reproduced from stolons at nurseries near Kalamazoo, Michigan.

The distinctive characteristics of this new variety of mint plant comprise its generally intermediate physical characteristics between its two parents, its high resistance to certain diseases as compared with *Mentha arvensis* L. *piperascens* Briq., its generally more fleshy and less fragile nature than either of its parents, its hardy nature under southern Michigan and central Washington field conditions and, especially, the extremely high total menthol content of its oil as compared with *Mentha piperita* L. The colors of the leaves and flowers are not distinctive features of this variety since they resemble closely the colors of the leaves and flowers of both parents. The stems are inclined to have a somewhat reddish tinge closely resembling that of the stems of *Mentha piperita* L. although this appears to be dependent, both in the new variety and in *Mentha piperita* L., at least to some extent, upon cultural conditions.

Specifically, the leaves of the new variety are opposite and intermediate in size, shape, indentation and hairiness between *Mentha arvensis* L. *piperascens* Briq. and *Mentha piperita* L. The leaves are broader at the base and more ovate than those of *Mentha arvensis* L. *piperascens* Briq. The leaf serrations are deeper than those of either parent and extend along the edge of the leaf practically to the leaf petiole, the lobes between the serrations being sharp and pointed. The new variety is somewhat more leafy than *Mentha arvensis* L. *piperascens* Briq. although not more so than *Mentha piperita* L. The plant is erect and somewhat reclining although less reclining than *Mentha piperita* L. and less erect than *Mentha arvensis* L. *piperascens* Briq. The flowers of the new variety are borne in somewhat globular axillary clusters extending down the stem for a considerable distance and in this respect resemble the flowers of *Mentha arvensis* L. *piperascens* Briq. rather than the terminal spikes of *Mentha piperita* L.

This new variety is immune to spearmint rust frequently identified as *Puccina menthae*, is much more resistant to powdery mildew, *Erysiphe cichoraccarum* D. C., than *Mentha arvensis* L. *piperascens* Briq. and is highly resistant to attack by *Cephalosporium sp.*, and various other unidentified leaf spot diseases which attack *Mentha arvensis* L. *piperascens* Briq.

The resistance of the new variety to these organisms was demonstrated in field plots on upland soil near Mentha, Michigan. Disease conditions were accentuated by interplantings of *M. arvensis* L. *piperascens* Briq. and of *M. citrata* Ehrh., *M. piperita* L., *M. cardiaca* (Gerarde or Baker?), *M. spicata* L. and other susceptible wild species as well as of a number of susceptible hybrid varieties under test. Mildew conditions were accentuated by shaking and spreading greenhouse grown *M. arvensis* L. *piperascens* Briq. heavily infested with powdery mildew over the plot. A similar second plot was planted the next year adjacent the first with stock taken from the first plot. The first year's plot was left unplowed, the plants in it being permitted to grow undisturbed the second year to furnish additional continuing inoculation of the second plot.

Susceptible varieties in both plots, including *M. arvensis* L. *piperascens* Briq., were heavily infested with mildew and leaf spot diseases, including *Cephalosporium sp.* Spearmint rust infestation was heavy in both plots, the susceptible varieties becoming 90 to 100 percent defoliated. The new variety was not attacked by spearmint rust in either plot and only to an insignificant extent by powdery mildew and leaf spot diseases.

Similar test procedures as regards powdery mildew and leaf spot diseases were carried out near Toppenish, Washington, under conditions of both overhead and ditch irrigation with comparable results.

The new variety is particularly remarkable for the high total menthol content of its oil as compared with *Mentha piperita* L. and other varieties of mint which are sufficiently hardy for field cultivation under southern Michigan conditions. The oil of the new variety invariably contains more than 70 percent, usually from 73 to 82 percent, of total menthol, as determined by the method for total menthol content given in the United States Pharmacopoeia No. 14. This compares with an average total menthol content of *Mentha piperita* L. of from 55 to 65 percent. The menthol present as esters in the new variety is generally from 3 to 6 percent of the total menthol content.

In the drawings, which are photographic illustrations of the new variety:

Figure 1:
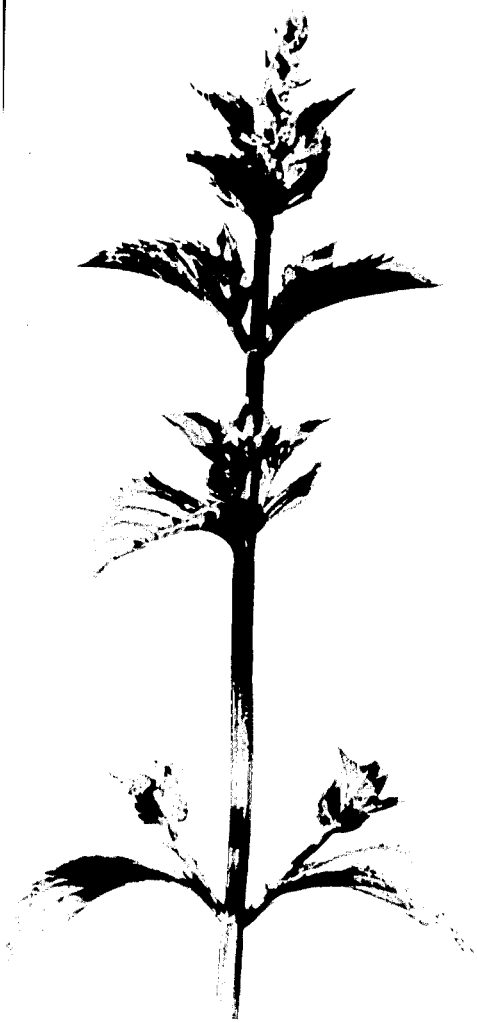
Figure 1 is a view of a budding branch of the new variety.
Figure 2:
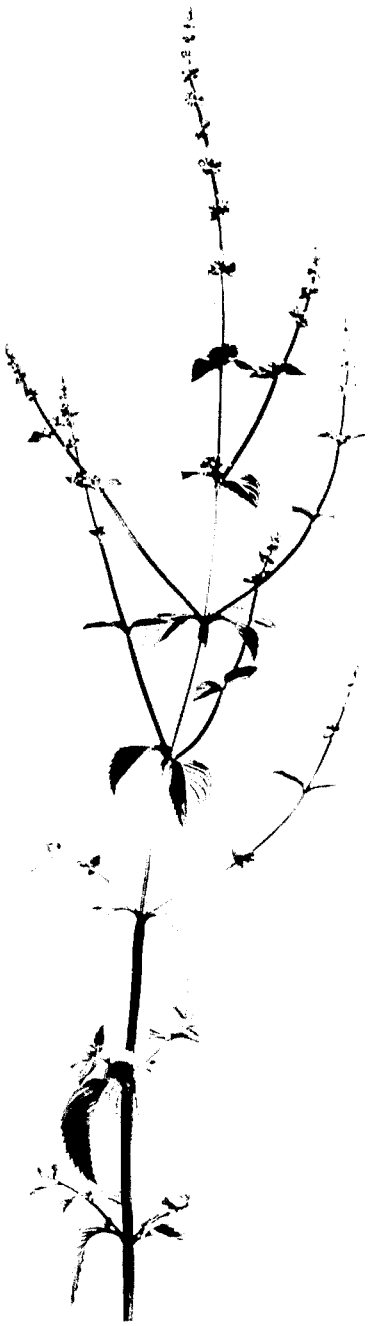
Figure 2 is an enlarged view of a flower stem illustrating the habit of the new variety of bearing its flowers in axillary clusters.

The hybridization was carried out in the summer of 1951 and the new variety was first reproduced asexually from stolons in the summer of 1952. Several thousand hybridizations of mint plants of various varieties were made at approximately the same time and from these it became apparent over the next year or two that the new variety herein described showed promise of being of commercial value. During September of 1953 the new variety described herein was propagated from stolons under field conditions near Kalamazoo, Michigan, and it has been grown in this manner since that time. It has consistently exhibited its hardy characteristics under climatic conditions favorable to the growth of *Mentha piperita* L. and the high total menthol content of its oil referred to previously.

I claim:

A new and distinct variety of mint plant substantially as described, characterized particularly by its hardy nature under adverse climatic conditions as compared with *Mentha arvensis* L. *piperascens* Briq. and by the high total menthol content of its oil as compared with *Mentha piperita* L.

No references cited.